United States Patent [19]

Swaisgood

[11] 4,087,328

[45] * May 2, 1978

[54] PURIFICATION AND IMMOBILIZATION OF SULFHYDRYL OXIDASE

[75] Inventor: Harold E. Swaisgood, Raleigh, N.C.

[73] Assignee: Research Triangle Institute, Reasearch Triangle Park, N.C.

[*] Notice: The portion of the term of this patent subsequent to Oct. 11, 1994, has been disclaimed.

[21] Appl. No.: 621,630

[22] Filed: Oct. 10, 1975

[51] Int. Cl.$^2$ ................... C12D 13/10; C07G 7/02; A23C 3/02; A23C 9/12
[52] U.S. Cl. ......................... 195/63; 195/66 R; 195/68; 195/DIG. 11; 195/116; 426/42; 426/330.2; 426/522
[58] Field of Search ................... 195/62, 66, 63, 68, 195/DIG. 11; 426/34, 42

[56] References Cited

U.S. PATENT DOCUMENTS

| | | | |
|---|---|---|---|
| 2,482,724 | 9/1949 | Baker | 426/42 X |
| 2,788,283 | 4/1957 | Stewart, Jr. et al. | 425/522 X |
| 3,282,702 | 11/1966 | Schreiner | 195/68 X |
| 3,627,640 | 12/1971 | Blumberg et al. | 195/63 |
| 3,705,084 | 12/1972 | Reynolds | 195/63 |

OTHER PUBLICATIONS

Swaisgood et al., Immobilization of Sulfhydryl Oxidase and some of its Kinetic Properties, J. Da. Sci., vol. 58, No. 5, May 1975 (p. 796).

Janolino, et al., Isolation and Characterization of Sulfhydryl Oxidase from Bovine Milk, The Journal of Biological Chemistry, vol. 250, No. 7, 4/10/75 (pp. 2532-2538).

*Primary Examiner*—David M. Naff
*Attorney, Agent, or Firm*—Cushman, Darby & Cushman

[57] ABSTRACT

Sulfhydryl oxidase is isolated in substantially purified form by precipitating from whey a crude impure fraction of sulfhydryl oxidase, dissolving the crude sulfhydryl oxidase in a dilute neutral buffer solution, equilibrating to allow for dissociation of the dissolved sulfhydryl oxidase, separating the equilibrated sulfhydryl oxidase from molecularly larger materials, concentrating the resultant separated sulfhydryl oxidase and separating the concentrated sulfhydryl oxidase from molecularly smaller materials to isolate a substantially purified sulfhydryl oxidase enzyme having a specific activity at least about fifty times greater than the crude enzyme and about 3000 times greater than that in skim milk. The enzyme may be immobilized, for example, by attaching it to an inert support. Activity of the immobilized enzyme may be regenerated by treatment with an aqueous solution of ferrous ions.

8 Claims, No Drawings

PURIFICATION AND IMMOBILIZATION OF SULFHYDRYL OXIDASE

BACKGROUND OF THE INVENTION

The invention described herein was made in the course of work under a grant from the National Science Foundation.

An enzymatic activity in milk which is characterized by its activity to oxidize sulfhydryl groups of cysteine, glutathione (GSH), and milk proteins to corresponding disulfides has been demonstrated by Freidrick Kiermeier and Ernst Petz [*Z. Lebensm.-Unters.-Forsch.*, Vol. 132, pages 342-351 (1967); and Vol. 134, pages 97-102 and 149-156 (1967)]. The reactions catalyzed by the crude preparations were suggested to be given by the equation:

$$2RSH + \tfrac{1}{2} O_2 \rightarrow RSSR + H_2O.$$

In accordance with the general rules for systematic and trivial nomenclature, they termed the enzyme sulfhydryl oxidase.

The crude enzyme was obtained by Kiermeier and Petz from the whey fraction of skim milk. Their attempts to purify and isolate the sulfhydryl oxidase enzyme were unsuccessful.

I have now found a method for isolating and purifying sulfhydryl oxidase enzyme from milk which consistently yields preparations of greater than 3000-fold purification over skim milk. Sulfhydryl oxidase in a substantially purified form has been found to catalyze the oxidation of sulfhydryl groups in both small compounds and proteins using oxygen as an oxidant. The enzyme in a substantially purified as well as immobilized form has been found useful in treating milk to remove the cooked flavor therefrom as described in my copending U.S. application Ser. No. 621,631, filed concurrently herewith titled "PROCESS OF REMOVING THE COOKED FLAVOR FROM HEAT TREATED MILK USING IMMOBILIZED SULFHYDRYL OXIDASE ENZYME" (the entire contents of which is incorporated herein by reference). It also appears that the immobilized enzyme could be useful in the biosynthesis of disulfides in certain proteins.

Accordingly, it is the primary object of my invention to provide a method for purifying and isolating sulfhydryl oxidase enzyme from milk.

It is a further object of my invention to provide a substantially purified sulfhydryl oxidase enzyme having a specific activity which is substantially and surprisingly greater than that found in previous crude enzyme preparations.

A still yet further object of the present invention is to provide a substantially pure sulfhydryl oxidase enzyme in an immobilized form.

Still yet a further object of my invention is a means by which the activity of substantially pure sulfhydryl oxidase in immobilized form may be maintained and rejuvenated.

And still another object of the present invention is to provide a means for providing a sulfhydryl oxidase enzyme having a specific activity at least 100 times greater than that of skim milk.

These and other objects of the present invention will be more readily apparent from the description which follows.

SUMMARY OF THE INVENTION

According to the present invention, sulfhydryl oxidase enzyme is isolated in a substantially purified from by a process comprising:

(a) obtaining a crude impure enzyme fraction of sulfhydryl oxidase from raw whole milk;

(b) dissolving the crude impure enzyme fraction in a dilute neutral buffer solution;

(c) equilibrating the solution of impure enzyme fraction;

(d) subjecting the impure enzyme fraction to a separation treatment to separate a first enzyme fraction from molecularly larger materials;

(e) concentrating the first enzyme fraction to obtain a second enzyme fraction; and (f) separating the second enzyme fraction to remove molecularly smaller materials and isolating the enzyme therefrom.

The sulfhydryl oxidase enzyme which is so isolated is in a substantially purified form. The term "substantially purified form" as used herein relates to sulfhydryl oxidase having a specific activity of at least 50 times greater than that of the crude enzyme fraction obtained in the whey fraction separated from skim milk obtained from whole raw milk. Specific activity as used herein is defined as the rate of catalysis per weight of enzyme. The crude enzyme fraction may be obtained in a manner similar to that disclosed by Kiermeier and Petz. Whole raw milk is treated to obtain skim milk (i.e. removing fat from solids not fat). The skim milk is then treated to obtain the whey by coagulation of the casein therein with rennin. The whey is cooled and ammonium sulfate is added in an amount to achieve one-half saturation. The precipitate which subsequently forms is referred to herein as the crude impure enzyme fraction.

The crude impure enzyme is processed to yield a substantially purified form of sulfhydryl oxidase which may be further treated to achieve a specific activity at least about 100 times greater than that of the crude enzyme fraction. The isolated enzyme obtained as noted above is dissolved in a neutral buffer solution to form a third enzyme fraction. The enzyme is then separated from molecularly smaller materials and isolated therefrom and exhibiting increased specific activity from the isolated form above.

DESCRIPTION OF THE PREFERRED EMBODIMENTS

Isolation of substantially pure sulfhydryl oxidase yields an enzyme which surprisingly possesses at least 1400 times the specific activity of that found in skim milk.

As an initial step, whole raw milk is treated to remove the fat from solids not-fat and obtain skim milk. Whey is obtained from the skim milk by coagulation of the casein fraction with rennin. The whey is removed, cooled and added to a half-saturated solution of ammonium sulfate to precipitate the crude enzyme. Previous prior attempts by otherst to isolate the enzyme by such means as gel chromatography have been unsuccessful. Further treatment according to this invention has been successful.

The crude enzyme fraction obtained as above is dissolved in a dilute neutral buffer solution (e.g. a phosphate buffer) in order to keep the enzyme stable. The enzyme in solution is then allowed to equilibrate (period to allow for dissociation of the enzyme) preferably under refrigerated conditions.

The solution is then subjected to a separation treatment (e.g. centrifugation) to separate the enzyme fraction from molecularly larger materials. Upon centrifugation of the solution the enzyme fraction is removed with the supernatant liquid. The supernatant liquid is then concentrated to from about 2½ to 3½% protein concentration by such means as for example an ultrafilter. However, other means such as addition of dry molecular sieves, or vacuum evaporation appear to be equally suitable. A concentration of at least about 2½% appears to be necessary in order to increase the enzyme molecule size by reassociation. The enzyme fraction is recovered in pellet form (for example by centrifugation) thereby achieving separation from molecularly smaller materials. The active enzyme fraction isolated in the resulting pellet possesses a specific activity at least about 1400 times greater than that of skim milk.

Increased specific activity of the enzyme is obtained by dissolving the pellet containing the above enzyme fraction in a neutral buffer solution at about twice the dilution (liquid volume) and subjecting the resulting solution to a separation treatment to obtain an even purer form of the enzyme having as much as a 3000-fold increase in specific activity over that of skim milk.

The isolated substantially purified sulfhydryl oxidase may be stored while refrigerated at about 4° C. without significant loss in activity. It is preferred to immobilize the isolated substantially purified sulfhydryl oxidase. Otherwise, the enzyme becomes an integral part of the reaction mixture and cannot be recovered following completion of the reaction. Enzyme immobilization is the process of modifying the enzyme molecule to restrict its movement and maintain it within a limited space. This may be accomplished by a variety of methods such as: absorption of the enzyme onto an insoluble carrier; entrapment or inclusion of it inside gel matrices; covalent chemical coupling to insoluble supports; and intermolecular crosslinking of the enzyme molecule.

A preferred means of immobilizing the isolated sulfhydryl oxidase according to the present invention is to attach the enzyme to glass beads. A suitable method is described in *Biochim. Biophys. Acta,* pages 243–256 (1974). Since immobilized sulfhydryl oxidase is activity sensitive to bacteria, heat, pH and dryness, it is essential that in storage in enzyme be prevented from drying out. Preferably the immobilized sulfhydryl oxidase is maintained in a neutral buffer solution (phosphate buffer) under refrigeration until ready for use.

The following examples are provided to more fully illustrate the invention, but are not to be construed as limiting the scope thereof.

EXAMPLE 1

Purification of sulfhydryl oxidase from bovine milk which consistently yields greater than 1400-fold purification over skim milk is achieved according to the following procedure. A concentration-dependent association dissociation of the enzyme was adapted to the following isolation procedure.

Materials — Fresh raw milk was collected directly in glass containers at the afternoon milking from individual cows and immediately cooled and stored at 4°. Enzyme grade sucrose and ammonium sulfate were obtained from Schwarz/Mann. Acrylamide, N,N'-methylenebisacrylamide, N,N,N',N'-tetramethylethylenediamine, 2-mercaptoethanol, and sodium dodecyl sulfate were purchased from Eastman (Rochester, N.Y.). D-Galactose, D-galactosamine (grade I), L-fucose, N-acetylneuraminic acid, EDTA, o-dianisidine, GSH, DTNB (5,5'-dithiobis/2 nitro benzoic acid) and glutathione reductase (type III) were products of Sigma (St. Louis, Mo.). Horseradish peroxidase (Worthington peroxidase D), RNase A (crystallized five times), and yeast RNA were purchased from Worthington (Freehold, N.J.), and crystalline rennin was obtained from Pierce (Rockford, Ill.). All metal and buffer salts were Baker reagent grade products.

A crude impure enzyme fraction prepared in a manner similar to that previously described by Kiermeier and Petz was used as a starting material. Accordingly, skim milk was prepared from whole raw milk by centrifugation at 4,080 × g for 30 minutes at 30°. Whey (Fraction B) was obtained from the skim milk by coagulation of the casein fraction with rennin. Approximately 2 mg of rennin were added per 100 ml of skim milk, and the reaction was allowed to proceed for 30 minutes at 30°. Under these conditions, only the Phe 105-Met 106 bond of k-casein is hydrolyzed (25). The resulting curd was removed by centrifuging at 16,300 × g for 45 minutes at 30°. The whey was cooled and immediately adjusted to one-half saturation in ammonium sulfate at 4°. After standing overnight at 4°, the precipitate (crude enzyme, Fraction C) was removed by centrifugation at 16,300 × g for 60 minutes at 4°.

Crude enzyme (Fraction C) was dissolved in 0.047 M sodium phosphate at pH 7.0 to give a concentration of 3% protein, and dialyzed against the same buffer at 4°. This solution was diluted with the buffer to 0.15% protein and allowed to stand overnight at 4°. Rapidly sedimenting impurities (Fraction D) were removed by centrifuging at 2000 × g for 30 minutes at 4°, and the resulting supernatant liquid (Fraction E) was concentrated in a 4° cold room to approximately 3% protein with an Amicon TCF-10 ultrafiltration system using an Amicon PM-10 membrane. This solution was again centrifuged at 2000 × g for 30 minutes at 4°, but this time the enzymatic activity appeared in the pellet (Fraction F).

The pellet represented sulfhydryl oxidase in a substantially purified form.

EXAMPLE 2

Smaller proteins present in Fraction F of Example 1 were removed by dissolving the pellet in twice the volume of the previous solution, allowing the solution to stand overnight at 4° to promote dissociation, and repeating the centrifugation at 2000 × g for 30 minutes at 4°. The resulting pellet (Fraction H) was taken as the purified enzyme.

Characteristics of fractions obtained in various steps of this procedure are listed in Table I. Activity was determined from the rate of $O_2$ consumption as measured by an oscillating platinum electrode using 0.8 mM GSH as substrate. One unit of activity is defined as 1 $\mu$mol of $O_2$ consumed per minute in phosphate buffer at pH 7.0 and 35°.

Activity Assay — Two methods of assay were developed, one based on disappearance of sulfhydryl groups, and the other on $O_2$ depletion. In the first, the concentration of sulfhydryl groups was measured by reaction with DTNB. In a typical assay, the reaction mixture contained 1.5 ml of 0.8 mM GSH in 0.047 M sodium phosphate at pH 7.0 (0.1 ionic strength) and 0.2 ml of enzyme solution. The control was identical except for the substitution of 0.2 ml of previously boiled enzyme solution for the native enzyme. Following incubation at 35°, aliquots of 0.3 ml were removed at various times and added to 9.7 ml of 0.017 M sodium phosphate at pH 8.0. From the resulting solutions, 3 ml were removed and mixed with 20 μl of 0.01 M DTNB in 0.047 M sodium phosphate, pH 7.0. The absorbance of this solution was measured at 412 nm after 2 minutes. The rate of the enzyme-catalyzed reaction was determined from the linear portion of a plot of sulfhydryl concentration versus time.

In the second method of assay, the rate of $O_2$ consumption was measured with an oscillating platinum electrode using a Gilson model K Oxygraph. In a typical assay, 0.2 ml of enzyme solution was added to 1.5 ml of 0.8 mM GSH which had been equilibrated at 35° in the electrode cell. Controls containing boiled enzyme exhibited no $O_2$ consumption. Enzymic reaction rates were calculated from the initial slopes obtained.

TABLE I

Purification of bovine sulfhydryl oxidase

| Fraction | Volume ml | Total activity units | Specific activity units/mg N | Recovery % |
|---|---|---|---|---|
| Skim milk | 1000 | 160.0 | 0.032 | 100 |
| Rennin whey | 930 | 153.9 | 0.174 | 96 |
| Crude enzyme (Fraction C) | 40 | 151.4 | 0.756 | 95 |
| First centrifugal pellet (Fraction F) | 80 | 96.0 | 47.1 | 60 |
| Second centrifugal pellet (Fraction H) | 24 | 65.1 | 103.8 | 41 |

Fraction F displayed considerably more activity than Fraction C. Gel chromatography of Fraction F gave only the fraction eluting in the void volume. Assays of protein eluted from the positions of each of the bands in an unstained gel showed that enzymic activity occured only at the top of the spacer gel and at the interface of the spacer and separation gels. Those proteins from Fraction F which appeared in the separation gels were effectively removed by centrifuging a slightly more dilute solution. Only two bands, both of which were enzymically active, were detectable upon gel electrophoresis of Fraction H. Furthermore, only one protein-staining band was visible following disc gel electrophoresis of this fraction in sodium dodecyl sulfate.

This method of purification is described in an article by Janolino and Swaisgood entitled "Isolation and Characterization of Sulfhydryl Oxidase from Bovine Milk", *J. of Biol. Chem.*, Vol. 250, No. 7, pp. 2532–2538 (Apr. 10, 1975).

It appears that iron is an integral part of the enzyme. Treatment of the enzyme with EDTA resulted in complete loss of activity which could be subsequently restored by dialysis against 1 μM ferrous sulfate. Furthermore, atomic absorption analysis and neutron activation analysis of separate enzyme preparations each indicated 0.5 atom of iron per subunit.

Contrary to the suggestions of Kiermeier and Petz noted above, I have found from studies of the stoichiometry of reactions catalyzed by sulfhydryl oxidase that the reaction actually catalyzed is that of an "aerobic oxidase" according to the equation:

$$2 RSH + O_2 \rightarrow RSSR + H_2O_2$$

The methods of Examples 1 and 2 have been repeated numerous times resulting in a reproducible product which represents greater than a 1400–3000 fold increase in specific activity over skim milk.

EXAMPLE 3

The temperature and pH dependence of the activity of the purified enzyme obtained in Example 2 were examined using GSH as substrate. Maximum activity was observed at a temperature of 35°. A symmetrical, bell-shaped dependence of activity on pH was observed, with a pH optimum of 6.8 to 7.0, and apparent $pK_a$ values of 5.5 and 8.1 governing the ascending and descending limbs, respectively. 0.2 ml of enzyme solution was added to 1.5 ml of 0.8 mM GSH which had been equilibrated at 35° in the electrode cell. Controls containing boiled enzyme exhibited no $O_2$ consumption. Enzymic reaction rates were calculated from the initial slopes obtained.

Subunit molecular weight studies were conducted on the purified enzyme obtained according to Example 2. The purified preparations of Example 2 exhibited two zones, both of which displayed activity, upon polyacrylamide disc gel electrophoresis, but only one zone following disc gel electrophoresis in sodium dodecyl sulfate. Sulfhydryl oxidase was examined using a series of acrylamide concentrations. Average apparent molecular weights from a number of experiments with the purified enzyme were determined to be 91,200 ± 1,200, 89,800 ± 800, 89,000 ± 400, and 89,000 ± 1,400 at 5.0, 7.5, 10.0, and 12.5% acrylamide concentrations, respectively. For each concentration, the calibration plot of the logarithm of the molecular weight versus mobility was essentially linear. At 10 and 12.5% acrylamide concentrations the values obtained for four independent preparations of the enzyme were in very good agreement, yielding an average subunit weight of 89,000 ± 900. In each case, a single protein band was observed at varying gel concentrations and enzyme loadings.

Chemical composition studies were also conducted using amino acid analysis as well as carbohydrate analysis. The amino acid analysis was conducted by weighing lyophilized samples of the purified enzyme into heavy walled ignition tubes and constant boiling (approximately 6N) HCl was added; the resulting solutions were frozen, deaerated, and the tubes were evacuated and sealed. Percentage of moisture in the lyophilized samples was determined by drying to constant weight at 75° in vacuo over $P_2O_5$. Hydrolysis was effected in a refluxing toluene bath for 16, 24, 48, and 72 hours, and hydrolysates were analyzed using a Beckman Model 116 amino acid analyzer.

Half-cystine content was determined independently as cysteic acid following performic acid oxidation. Tryptophan was estimated by chromatographic analysis following enzymatic hydrolysis with pronase.

According to the carbohydrate analysis, total hexose content was determined by the phenolsulfuric acid method. Following hydrolysis in 0.1 N HCl at 80° for 1 hour, sialic acid was measured by Aminoff's procedure using an N-acetylneuraminic acid standard. Hexosamine was quantitated after hydrolysis in 2 N HCl at 100° for 16 hours. Galactosamine was employed as a standard and the values reported as N-acetylhexosamine. Fucose (6-deoxy-I.-galactose) was estimated by the thioglycolic acid-sulfuric acid method with focuse as a standard.

Results of amino acid and carbohydrate analyses are listed in Table II. These data indicate that essentially all of the sample weight (97%) is accounted for by amino acid and carbohydrate residues, of which 89% is represented by amino acid residues and 11% by carbohydrate.

TABLE II

Amino acid and carbohydrate composition of purified sulfhydryl oxidase

Amino acid values reported are averages of 16-, 24-. 48- and 72-hour hydrolysis times, except for Th, Ser, Val, Ile, Lev, Tyr, and Trp. Values for Thr, Ser, and Tyr were obtained by extrapolation to zero hydrolysis time, those for Val, Ile, and Leu by extrapolation to infinite hydrolysis time. The value for Half-Cys was corrected for assumed 95% recovery of cysteic acid following performic acid oxidation. Trp was determined following Pronase digestion.

| Component | μmoles/mg | Residue g/100 g | Number/89000 g | Nearest integer |
|---|---|---|---|---|
| Amino acids | | | | |
| Lys | 0.504 ± .014 | 6.46 | 44.9 | 45 |
| His | 0.124 ± .004 | 1.70 | 11.0 | 11 |
| Arg | 0.332 ± .012 | 5.19 | 29.5 | 30 |
| Asp | 0.698 ± .001 | 8.03 | 62.1 | 62 |
| Thr | 0.475 | 4.80 | 42.3 | 42 |
| Ser | 0.519 | 4.52 | 46.2 | 46 |
| Glu | 0.811 ± .018 | 10.47 | 72.2 | 72 |
| Pro | 0.416 ± .010 | 4.04 | 37.0 | 37 |
| Gly | 0.845 ± .035 | 4.83 | 75.2 | 75 |
| Ala | 0.967 ± .026 | 6.88 | 86.1 | 86 |
| Half-Cys | 0.061 ± .001 | 0.63 | 5.4 | 5 |
| Val | 0.630 | 6.24 | 56.1 | 56 |
| Met | 0.082 ± .044 | 1.08 | 7.3 | 7 |
| Ile | 0.360 | 4.08 | 32.0 | 32 |
| Leu | 0.680 | 7.70 | 60.5 | 61 |
| Tyr | 0.203 | 3.32 | 18.1 | 18 |
| Phe | 0.326 ± .012 | 4.80 | 29.0 | 29 |
| Trp | 0.058 ± .005 | 1.08 | 5.2 | 5 |
| Carbohydrates | | | | |
| Fucose | 0.030 | 0.44 | 2.7 | 3 |
| Total hexose | 0.444 ± .002 | 7.19 | 39.5 | 40 |
| N-Acetylhexosamine | 0.143 ± .002 | 2.90 | 12.7 | 13 |
| N-Acetylneuraminic acid | 0.013 | 0.41 | 1.2 | 1 |

EXAMPLE 4

Immobilization of the purified sulfhydryl oxidase obtained in Example 2 was achieved by affixing the enzyme to glass beads. Succinilate glass beads were prepared from γ-amino-propyl-glass beads (40–60 mesh, 2000A pore diameter) available from Corning Glass Works, which were then washed with distilled water and equilibrated for 24 hours in a 0.2 M phosphate buffer at pH 4.75. The beads were degassed and to 0.5 g of the beads crystalline 1-ethyl-3-dimethyl-aminopropyl carbodiimide (EDC) was added and the reaction was carried out for 20 minutes at 25° C and a constant pH of 4.75. The beads were then washed with distilled water and cold neutral phosphate buffer solution to remove excess EDC. The isolated enzyme (0.1% wgt/vol.) in a phosphate buffer solution was then contacted with the succinilate beads for between 16 and 24 hours after which the beads were washed with 0.1 M phosphate buffer of pH 7. This resulted in covalently coupling the isolated enzyme to the glass beads yielding an immobilized sulfhydryl oxidase. As previously noted, the immobilized enzyme when not in use should be prevented from drying out and subjected to extreme temperatures by storage under refrigeration in a phosphate buffer solution of pH 7.

EXAMPLE 5

Reactivation of immobilized sulfhydryl oxidase is achieved by contacting the deactivated immobilized enzyme with an aqueous solution of ferrous sulfate. As previously noted iron appears to be an integral part of sulfhydryl oxidase. Treatment of the enzyme with EDTA resulted in complete loss of activity as illustrated by the data in Table IV. Dialysis against 1 μM $Fe^{2+}$ restored 70% of the original activity. Some activity could also be restored by $Cu^{2+}$ (30%) or $Mn^{2+}$ (20%). The electronic absorption spectrum of the native enzyme exhibited a typical protein maximum at 278 nm ($E_1^{1\%}{}_{cm} = 7.41$), but no maxima at longer wavelengths; thus, it appears that iron is not present in the form of a heme prosthetic group. Calculations based on atomic absorption spectral analyses indicated the presence of 0.48 g. atoms of iron and approximately 0.15 g. atoms of copper per 89,000. Neutron activation analysis of a separate preparation gave $11.1 = 0.3$ μg of iron for a 38.5-mg sample, which corresponds to 0.46 g. atom of iron per 89,000. Copper could not be determined under the conditions employed, and analysis for other metals indicated only traces of zinc and cobalt. No molybdenum or manganese could be detected. Thus, iron appears to be required for the enzymatic activity of sulfhydryl oxidase.

TABLE IV

Effect of metal ions on sulfhydryl oxidase activity

Assays were performed in phosphate at pH 7.0 and 35° using 0.8 mM GSH as substrate. An aliquot of the stock enzyme solution was removed and assayed in the presence of 1.0 mM EDTA. Following treatment of other aliquots of the stock solution with EDTA, these were dialyzed against 1.0 mM solutions of the various metal ions. Controls were prepared using boiled enzyme and also using the dialysate containing the metal ion. In both cases, significant $O_2$ consumption was not observed.

| Treatment | Enzyme activity |
|---|---|
| | μmol $O_2$ consumed/min. |
| Sulfhydryl oxidase (control) Enzyme | 0.368 |
| + EDTA (1.0 mM) | 0.012 |
| + Ferrous sulfate | 0.256 |
| + Copper sulfate | 0.109 |
| + Manganese (II) chloride | 0.085 |
| + Cobalt chloride | 0.021 |
| + Zinc sulfate | 0.029 |
| + Molybdenum dibromide[a] | 0.008 |

[a]Although molybdenum dibromide was used to prepare the solution, it most likely oxidized to higher oxidation states.

From the foregoing discussion and examples, it can be seen that the successful isolation process according to my invention utilizes the concentration-dependent association-dissociation characteristics to yield an unexpectedly substantially pure enzyme having an unusually high degree of specific activity.

The invention in its broader aspects is not limited to the specific details shown and described, but departures may be made from such details within the scope of the accompanying claims without departing from the principles of the invention.

The invention may furthermore comprise, consist or consist essentially of the hereinbefore recited materials and steps.

I claim:
1. A process for isolating sulfhydryl oxidase enzyme from milk which comprises:
   (a) precipitating a crude impure enzyme fraction of sulfhydryl oxidase from the whey of skim milk;
   (b) dissolving said impure enzyme fraction in a dilute neutral buffer solution;

(c) equilibrating said impure enzyme fraction to allow for dissociation of the sulfhydryl oxidase;

(d) separating a first fraction of sulfhydryl oxidase enzyme from molecularly larger materials by subjecting the impure enzyme fraction from step (c) to a separation treatment;

(e) concentrating the first fraction of sulfhydryl oxidase enzyme obtained in step (d) by means of an ultrafilter, dry molecular sieves or vacuum evaporation to obtain a second fraction of sulfhydryl oxidase enzyme; and (f) separating said second fraction of sulfhydryl oxidase to remove molecularly smaller materials and isolating the sulfhydryl oxidase enzyme therefrom said sulfhydryl oxidase having a specific activity at least 50 times greater than that of the crude impure enzyme fraction obtained in step (a).

2. A process according to claim 1 wherein the isolated enzyme obtained in step (f) is dissolved in a neutral buffer solution to form a third enzyme fraction, further separating the enzyme from molecularly smaller materials and isolating the enzyme therefrom to obtain an enzyme of increased specific activity.

3. A method according to claim 1 wherein said first enzyme is concentrated in step (e) by means of an ultrafilter.

4. A process according to claim 1 wherein separation of said first and second enzyme fraction is by centrifugation.

5. A method according to claim 1 wherein the enzyme isolated in step (f) is immobilized on glass beads.

6. Immobilized and substantially purified sulfhydryl oxidase enzyme, said enzyme being obtained according to the process of claim 1 and characterized as having a specific activity of at least 50 times greater than that of the crude sulfhydryl oxidase enzyme fraction obtained in the whey fraction separated from skim milk obtained from whole raw milk.

7. A process for regenerating the activity of an immobilized sulfhydryl oxidase enzyme which comprises contacting said enzyme with an aqueous solution of ferrous ions.

8. A process according to claim 7 wherein said solution is aqueous ferrous sulfate.

* * * * *